United States Patent
Park

(10) Patent No.: US 6,675,393 B1
(45) Date of Patent: Jan. 13, 2004

(54) CAP WITH UNITARY CROWN AND VISOR FABRIC PORTION

(75) Inventor: Boo Yl Park, Seoul (KR)

(73) Assignee: DADA Corp.

( * ) Notice: Subject to any disclaimer, the term of this patent is extended or adjusted under 35 U.S.C. 154(b) by 0 days.

(21) Appl. No.: 10/228,088

(22) Filed: Aug. 27, 2002

(30) Foreign Application Priority Data

Jul. 15, 2002 (KR) .......................... 2002-21131

(51) Int. Cl.⁷ .............................................. A42B 1/00
(52) U.S. Cl. .............................................. 2/195.2; 2/12
(58) Field of Search .................. 2/12, 171, 209.11, 2/175.1–175.4, 195.1–195.5

(56) References Cited

U.S. PATENT DOCUMENTS

| | | | |
|---|---|---|---|
| 2,736,035 A | * 2/1956 | Spreiregen | ................... 2/195.6 |
| 4,023,212 A | 5/1977 | Huffman | |
| 4,131,953 A | 1/1979 | Kimotsuki | |
| 4,873,726 A | 10/1989 | Tapia | |
| 5,136,726 A | 8/1992 | Kellin et al. | |
| 5,901,370 A | 5/1999 | Linday | |
| 5,983,400 A | * 11/1999 | Kronenberger | ............. 2/209.13 |
| 6,357,051 B1 | * 3/2002 | Lee | ............................. 2/195.1 |
| 6,463,592 B1 | * 10/2002 | Brooks | ...................... 2/209.12 |

* cited by examiner

*Primary Examiner*—Katherine Moran
(74) *Attorney, Agent, or Firm*—Jacobson Holman PLLC

(57) ABSTRACT

Headwear having a head-fitting portion and a visor portion, with an extended fabric portion stretching from the top of the head-fitting portion to the front edge of the visor portion to create the appearance of a unitary crown and visor. The resulting headwear, which can include a baseball-style cap and a sun visor, can be produced easily and is attractive in use, enabling decorative portions to transition without interruption from the visor to and across the head-fitting portion.

14 Claims, 3 Drawing Sheets

FIG.1 - Prior Art

CAP WITH UNITARY CROWN AND VISOR FABRIC PORTION

BACKGROUND OF THE INVENTION

1. Field of the Invention

The present invention is related to the field of caps having visors and, more particularly, to headwear having extended fabric portions to create a crown and visor with unitary appearance.

2. Description of the Related Art

Baseball style caps, such as that shown in FIG. 1, are widely worn and generally include a crown 1 which is the main part of the cap, a visor 2 which is attached to the underside of the front part of the crown, and a size controlling part (not visible) which is attached to the inner edge of the rear part of the crown. The crown 1 is generally made of several triangular portions of cloth which are sewn together, while the visor 2 is generally made of two cloth sheets separated and reinforced by a fixing element.

When manufacturing a conventional baseball-style cap, such as that shown in FIG. 1, the crown and visor portions are made separately and then subsequently sewn together. Such separate manufacturing steps increase fabrication time and reduce productivity. If coordinating designs or decorative additions across the crown and visor portions are desired, fabrication time is further increased.

Therefore, a need exists for aesthetically pleasing headwear having simplified manufacturing requirements.

SUMMARY OF THE INVENTION

In view of the foregoing, one object of the present invention is to provide an improved cap structure having a unitary crown and visor fabric portion with simplified manufacturing requirements.

Another object of the present invention is headwear having extended fabric portions that create a unitary crown and visor appearance which allows decorative portions to be easily extended across the entire crown and visor areas without interruption.

A further object of the invention is headwear having a unitary design with linking embroidery for enhanced visual appeal.

In accordance with these and other objects, the present invention is directed to a cap having a crown, a visor, a headband and preferably a size adjusting part. The front portion of the crown is formed from one or more unitary pieces of fabric which extend from the upper button of the cap to the foremost edge portion of the visor. As a result, the entire external surface portion of the cap is constructed in the same step.

The present invention is also directed to a sun visor having a rim part and a visor part, and preferably also a size adjusting part. Extended fabric portions span from the front side of the rim part to the foremost edge portion of the visor to create a unitary external appearance ideal for a wide range of designs extending across the entire outer surface of the sun visor.

These together with other objects and advantages which will become subsequently apparent reside in the details of construction and operation as more fully hereinafter described and claimed, reference being had to the accompanying drawings forming a part hereof, wherein like numerals refer to like parts throughout.

DETAILED DESCRIPTION OF THE PREFERRED EMBODIMENTS

Figure 1:
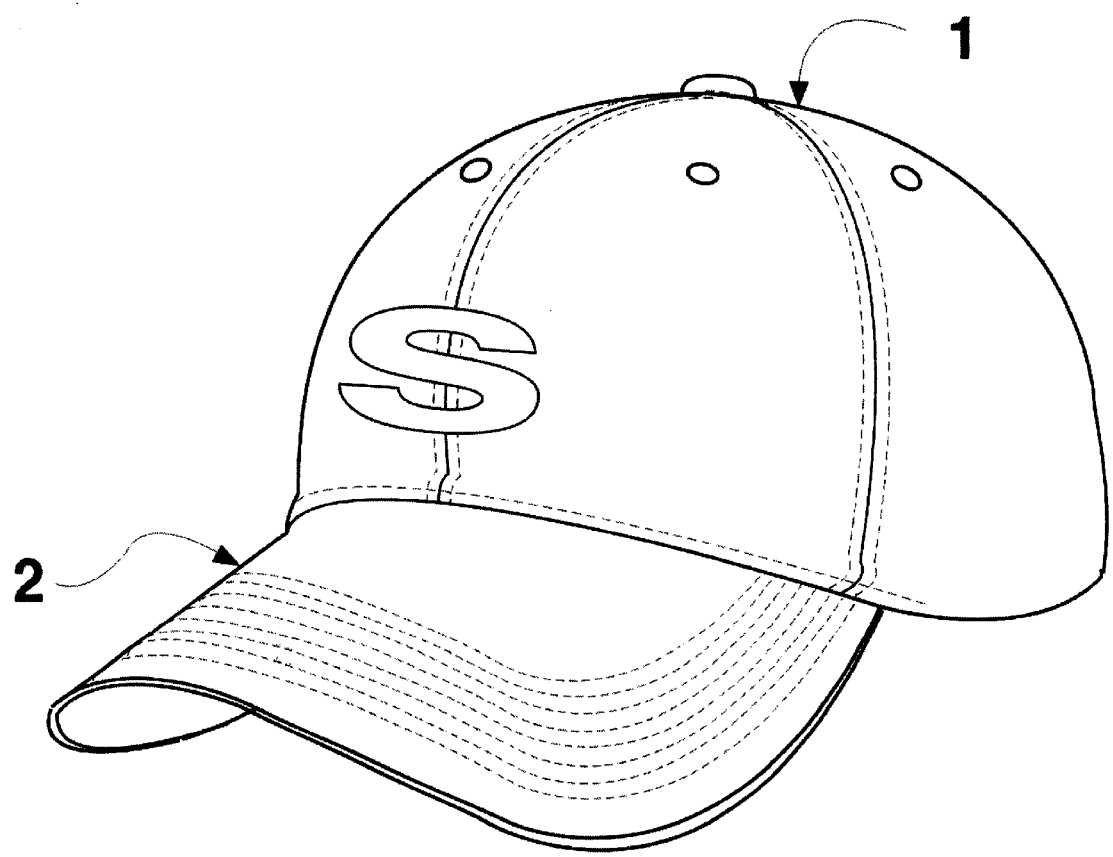
FIG. 1 is a perspective view of a conventional cap.

In describing a preferred embodiment of the invention illustrated in the drawings, although only two preferred embodiments of the invention are explained in detail, it is to be understood that these embodiments are given by way of illustration only. It is not intended that the invention be limited in its scope to the details of construction and arrangement of components set forth in the following description or illustrated in the drawings. Also, in describing the preferred embodiments, specific terminology will be resorted to for the sake of clarity. It is to be understood that each specific term includes all technical equivalents which operate in a similar manner to accomplish a similar purpose.

Figure 2:
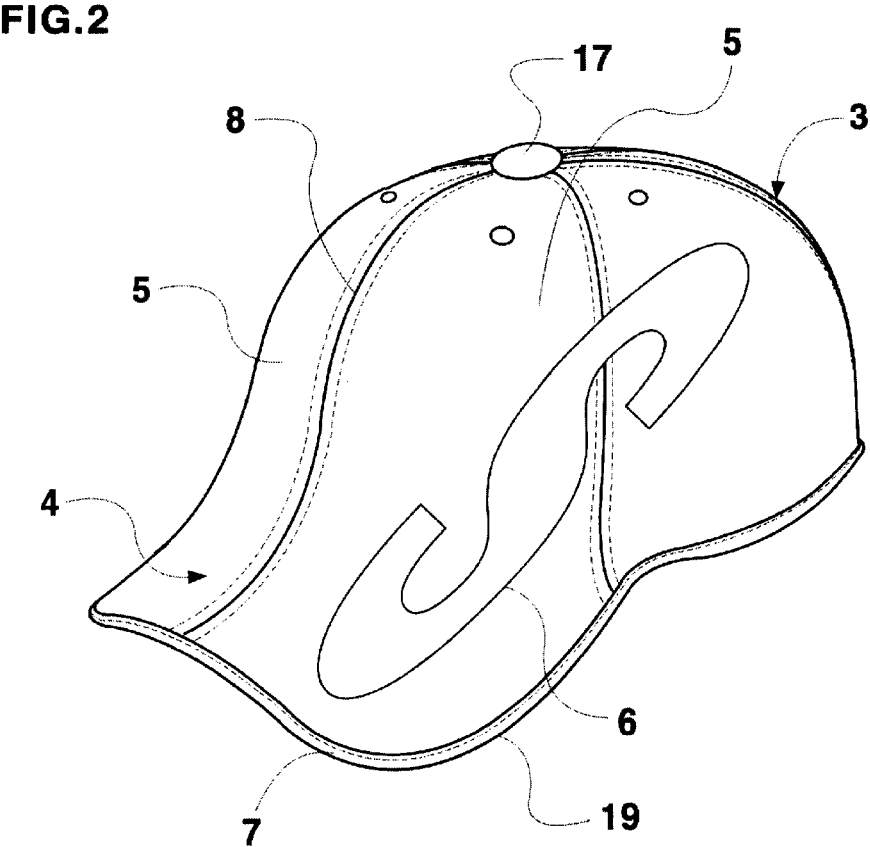
FIG. 2 is a perspective view illustrating a cap according to the present invention.

In accordance with a first preferred embodiment of the present invention, the present invention is directed to a baseball-style cap having a unitary crown and visor construction as illustrated in FIG. 2. As shown, the cap includes a crown part, generally designated by the reference numeral 3. The crown part is the main portion of the cap, and is constructed of a plurality of fabric portions which meet at the top and are typically covered by a button 17. The front portion of the crown part 3 is covered with one or more extended fabric portions 5 which extend from the button 17 to the front edge 7 of the visor part, generally designated by the reference numeral 4. As a result, the crown part 3 and the visor part 4 are seen as one unit, making the cap more fashionable and aesthetically pleasing. The extended fabric portions 5 are sewn on the front and side edges of the visor part with a cloth trim 19 so that the fabric covering the underside of the visor may be sewn to the extended fabric portions 5 and neatly covered. The cloth trim 19 is preferably a single unit, further enhancing the unitary appearance of the cap.

Unlike conventional hat designs, in which complicated procedures were necessary to effect separate embroidered portions for the crown and visor parts which would, when combined, demonstrate good linkage, with the present invention decorative designs 6 of any desired degree of intricacy, whether embroidered or otherwise affixed, can be expressed simply and naturally, flowing without interruption across the entire crown and visor area due to the unitary crown and visor extended fabric portions 5.

Figure 3:
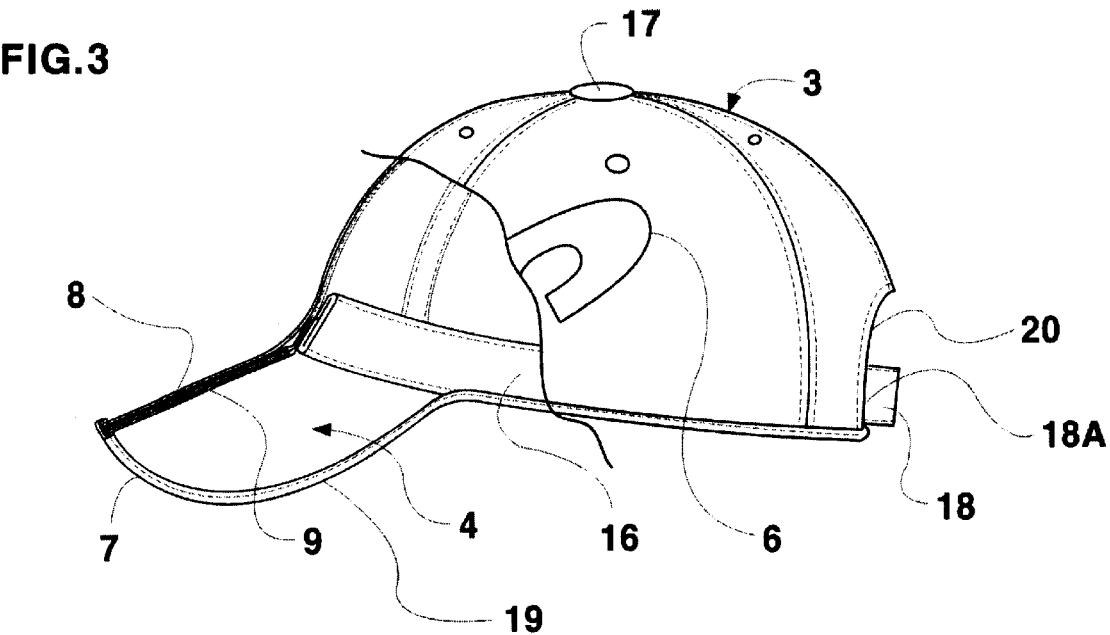
FIG. 3 is a partially sectioned view of the cap of FIG. 2.

FIG. 3 is a partial cross-sectional view of the cap of FIG. 2, with the extended fabric portions 5 running from the crown to the front edge 7 of the visor 4 and covered with the wrapping trim 19. The visor 4 includes a reinforced portion which is covered on the top with the extended fabric portions 5 and on the bottom with cloth 9. The headband 16 is stitched to the inside lower edge of the crown 3.

The rear side of the crown typically has a cutout portion 20 to provide for size adjustment in conjunction with size controlling portion 18. The size controlling portion 18 may be embodied as two strips of cloth or similar material, each sewn to a respective rear edge 18A and extending toward the other across the cutout portion 20. The size controlling portions 18 attach to one another through a hook and loop closure, snaps or with any other adjustable fastening means.

To stitch the visor part 4 to the front side of the crown 3, the extended fabric portions 5 are placed close to cloth 9 and seam 8 is sewn first. The work is finished by wrapping the edges, where the extended fabric portions 5 and the cloth 9 join, with trim 19 which is sewn to the underlying fabrics. The embroidery part 6 is sewn as a single unit along the extended fabric portions 5 prior to joining of the visor part 4 to the crown 3.

Figure 4:
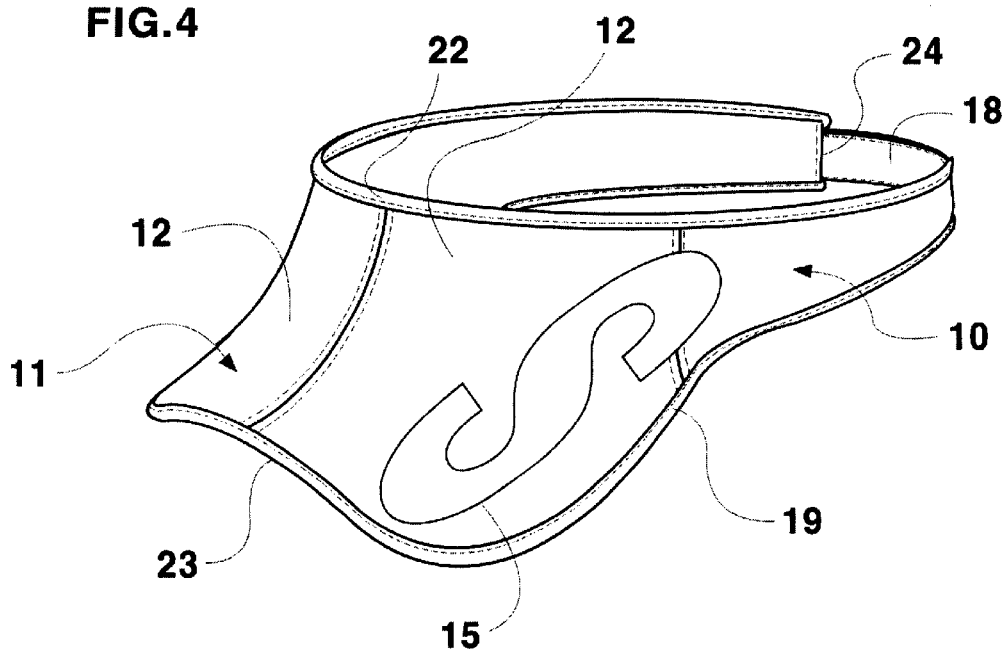
FIG. 4 is a perspective view illustrating a sun visor according to the present invention.
Figure 5:
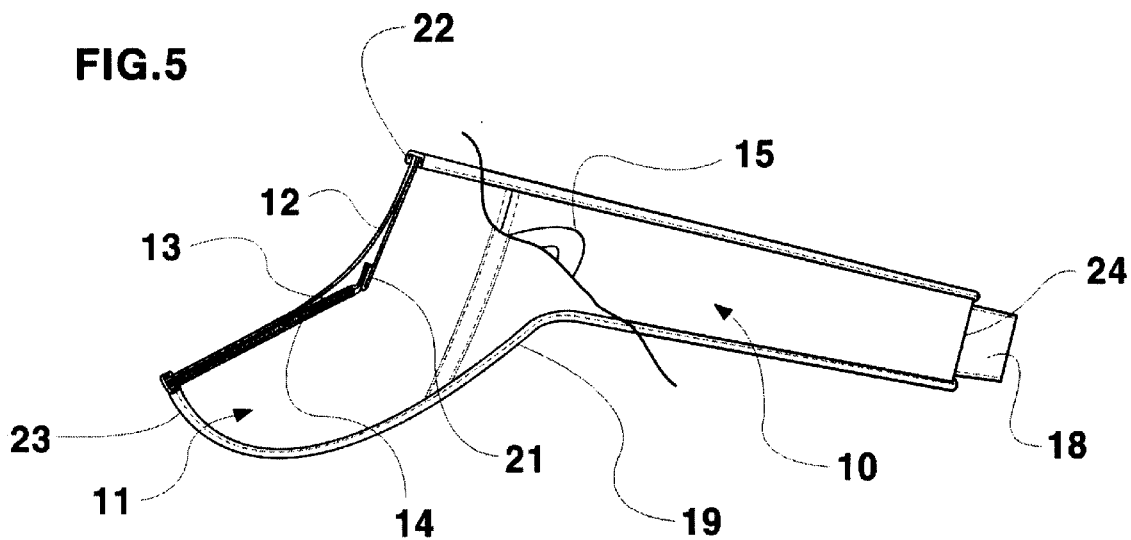
FIG. 5 is a partially sectioned view of the sun visor of FIG. 4.

A sun visor according to a second preferred embodiment of the invention is depicted in FIGS. 4 and 5. As illustrated, the sun visor includes a rim part, generally designated by the reference numeral 10, and a visor part, generally designated by the reference numeral 11.

The visor part 11 includes a reinforced portion 13 which is stitched to a lower edge 21 of the front side of the rim part 10 as shown in FIG. 5. On the upper side of the sun visor, extended fabric portions 12 span from the upper edge 22 of the front side of the rim part 10 to the front edge 23 of the visor part 11. The underside of the visor part 11 is covered with cloth 14, and the edge of the sun visor where the cloth 14 and the extended fabric portions are joined is covered with cloth trim 19 for a neat appearance. The cloth trim 19 is preferably a single unit, further enhancing the unitary appearance of the sun visor. A size controlling portion 18 is stitched to each of the rear side edges 24 of the rim part 10. The size controlling portions 18 attach to one another through a hook and loop closure, snaps or with any other adjustable fastening means.

As with the cap of FIGS. 2 and 3, because the extended fabric portions 12 cover the entire upper frontal portion of the headwear, the rim part 10 and the visor part 11 are seen as a single unit, enhancing the appearance of the design 15 depicted thereon. In addition, because the design is applied to the unitary extended fabric portion in a single step, no effort must be expended to coordinate separate visor and crown designs, such that the present invention simplifies and speeds manufacture.

The foregoing descriptions and drawings should be considered as illustrative only of the principles of the invention. The invention may be configured in a variety of shapes and sizes and is not limited by the dimensions of the preferred embodiments. Numerous applications of the present invention will readily occur to those skilled in the art. For example, the unitary crown and visor construction may be incorporated into hats and caps of other styles. Therefore, it is not desired to limit the invention to the specific examples disclosed or the exact construction and operation shown and described. Rather, all suitable modifications and equivalents may be resorted to, falling within the scope of the invention.

What is claimed is:

1. Headwear comprising:
    a head-fitting part;
    a visor connected to a lower edge of a front part of said head-fitting part, and having an inner periphery and an outer periphery, wherein the inner periphery is connected to the head-fitting part; and
    an extended fabric portion covering said visor and said front part such that no seams separate an upper edge of said head-fitting part from an outermost edge of said visor.

2. The headwear as set forth in claim 1, wherein said head-fitting part is a crown part and said headwear is a baseball-style cap.

3. The headwear as set forth in claim 1, wherein said head-fitting part is a rim part and said headwear is a sun visor.

4. The headwear as set forth in claim 2, further comprising a unitary embroidered design extending along said extended fabric portion such that said design extends from said visor to and across said head-fitting part without interruption.

5. The headwear as set forth in claim 3, further comprising a unitary embroidered design extending along said extended fabric portion such that said design extends from said visor to and across said head-fitting part without interruption.

6. The headwear as set forth in claim 1, wherein two extended fabric portions cover said visor and said front part, said two extended fabric portions joined by a seam extending from a center of said outermost edge to a top of said head-fitting part.

7. A baseball-style cap comprising:
    a crown main body;
    a headband sewn to an inner lower edge of said crown main body;
    a visor connected to a lower edge of a front part of said crown main body, having a lower fabric portion and a reinforced portion, said lower fabric portion sewn to said headband, and having an inner periphery and an outer periphery, wherein the inner periphery is connected to the crown main body; and
    an extended fabric portion on an upper side of said visor and covering said reinforced portion, said extended fabric portion extending uninterrupted from an outer edge of said visor to a top of said crown main body.

8. The cap as set forth in claim 7, further comprising a unitary embroidered design extending along said extended fabric portion such that said design extends from said outer edge of said visor to and across said crown main body without interruption.

9. The cap as set forth in claim 7, wherein two extended fabric portions cover said visor and a front part of said crown main body, said two extended fabric portions joined by a seam extending from a front center of said outer edge of said visor to said top of said crown main body.

10. The cap as set forth in claim 7, wherein a joining between the lower fabric portion and said extended fabric portion along said outer edge of said visor as well as a lower edge of said crown main body is wrapped with a unitary piece of cloth trim.

11. A sun visor comprising:
    a rim part;
    a visor connected to a lower edge of a front part of said rim part, having a lower fabric portion and a reinforced portion, said lower fabric portion sewn to an inner lower edge of said rim part, and having an inner periphery and an outer periphery, wherein the inner periphery is connected to the rim part; and
    an extended fabric portion on an upper side of said visor and covering said reinforced portion, said extended fabric portion extending uninterrupted from an outer edge of said visor to a top edge of said rim part.

12. The sun visor as set forth in claim 11, further comprising a unitary embroidered design extending along said extended fabric portion such that said design extends from said outer edge of said visor to and across said rim part without interruption.

13. The sun visor as set forth in claim 11, wherein two extended fabric portions cover said visor and a front part of said rim part, said two extended fabric portions joined by a seam extending from a front center of said outer edge of said visor to said top edge of said rim part.

14. The sun visor as set forth in claim 11, wherein a joining between the lower fabric portion and said extended fabric portion along said outer edge of said visor as well as a lower edge of said rim part is wrapped with a unitary piece of cloth trim.

* * * * *